US010835526B2

(12) United States Patent
Ahee

(10) Patent No.: US 10,835,526 B2
(45) Date of Patent: *Nov. 17, 2020

(54) ANTIBIOTIC SOLUTION AND METHOD OF INJECTION TO PREVENT OPHTHALMIC INFECTIONS

(71) Applicant: Jason Ahee, Ivins, UT (US)

(72) Inventor: Jason Ahee, Ivins, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/287,677

(22) Filed: Feb. 27, 2019

(65) Prior Publication Data

US 2020/0046691 A1  Feb. 13, 2020

Related U.S. Application Data

(63) Continuation of application No. 16/101,828, filed on Aug. 13, 2018, now Pat. No. 10,265,312.

(51) Int. Cl.
| | |
|---|---|
| *A61K 31/4709* | (2006.01) |
| *A61K 47/24* | (2006.01) |
| *A61P 27/02* | (2006.01) |
| *A61K 9/00* | (2006.01) |
| *A61K 9/08* | (2006.01) |
| *A61K 31/546* | (2006.01) |
| *A61K 49/00* | (2006.01) |
| *A61K 45/06* | (2006.01) |
| *A61K 38/14* | (2006.01) |

(52) U.S. Cl.
CPC ........ *A61K 31/4709* (2013.01); *A61K 9/0019* (2013.01); *A61K 9/0048* (2013.01); *A61K 9/08* (2013.01); *A61K 31/546* (2013.01); *A61K 45/06* (2013.01); *A61K 47/24* (2013.01); *A61K 49/0036* (2013.01); *A61P 27/02* (2018.01); *A61K 38/14* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,869,468 A | 2/1999 | Freeman | |
| 6,692,526 B1 * | 2/2004 | Snyder | A61F 9/0008 128/898 |
| 7,585,291 B1 * | 9/2009 | Campion | A61K 9/0048 604/289 |
| 10,265,312 B1 * | 4/2019 | Ahee | A61K 31/4709 |
| 2002/0193370 A1 | 12/2002 | Cagle et al. | |
| 2016/0235674 A1 | 8/2016 | McDonnell et al. | |
| 2016/0243031 A1 | 8/2016 | Wiley et al. | |

FOREIGN PATENT DOCUMENTS

WO    2018144786    8/2018

OTHER PUBLICATIONS

Haripriya et al. J Ophtha 123(2) (2016) p. 302-308. (Privided to Applicants in parent U.S. Appl. No. 16/101,828).*
Ng et al. Grafes Arch. Clin. Exp. Ophthalmol. (2016) 254: p. 1987-1992. (Privided to Applicants in parent U.S. Appl. No. 16/101,828).*
The Rational Behind Using Medical Regimens for Cataract Surgery, Healio News, p. 1-11, published on May 25, 2010. (Privided to Applicants in parent U.S. Appl. No. 16/101,828).*
Yamada et al. Nippon Ganka Gakkai Zasshi (1995); 99(3): 262-70.*
Kumar et al., J Clin Ophthalmol Res, (2013), 1(1), p. 55-58.*
Li et al. J Pharm Sci., (2012), 101(7), p. 2353-2363.*
Sue Stevens, Community Eye Health, (2009), 22(69), p. 15.*
Chan et al. "Cobalamin-Associated Superoxide Scavenging in Neuronal Cells is a Potential Mechansim for Vitamin B12-Deprivation Optic Neuropathy" The American Journal of Pathology. Jan. 1, 2018, vol. 188, p. 160-172.

* cited by examiner

*Primary Examiner* — Yong L Chu
(74) *Attorney, Agent, or Firm* — Gurr Brande & Spendlove, PLLC; Robert A. Gurr

(57) ABSTRACT

A method of preventing post-operative endophthalmitis involves injecting a colored antibiotic solution into the anterior segment of the eye during surgery, the antibiotic solution having moxifloxacin, cefuroxime, vancomycin, or some combination thereof, and the coloring agent being preferably a cobalamin (e.g., cyanocobalamin).

9 Claims, No Drawings

ANTIBIOTIC SOLUTION AND METHOD OF INJECTION TO PREVENT OPHTHALMIC INFECTIONS

CROSS-REFERENCE TO RELATED APPLICATIONS

This application is a continuation of prior non-provisional application Ser. No. 16/101,828 filed Aug. 13, 2018, now U.S. Pat. No. 10,265,312, which was a continuation-in-part of prior non-provisional application Ser. No. 15/886,807 filed Feb. 1, 2018, which claimed the benefit of U.S. Provisional Application Ser. No. 62/453,443 filed on Feb. 1, 2017, all of which are incorporated herein by reference.

TECHNICAL FIELD

The present disclosure relates to antibiotics for the eyes. More particularly, the present disclosure relates to antibiotic solutions that are injected into the eye (i.e., intracameral) during surgery.

BACKGROUND

Ocular surgeries are performed frequently by ophthalmologists, with special care and attention to the eye being required before, during, and after surgery. A possible complication of all intraocular surgeries is endophthalmitis, which is inflammation of the internal coats of the eye because of infection. Endophthalmitis is a serious condition that can cause blindness. Once present, a vitreoretinal specialist will usually provide an intravitreal injection of antibiotics, which may include vancomycin and ceftazidime. However, depending upon how long the eye was infected, the patient may still experience eye pain and require further surgeries. Therefore, avoiding endophthalmitis complications is preferable, with ophthalmologists using a variety of methods to lower the risk of infection.

To prevent endophthalmitis, the current standard of care includes using eye drops before and after the surgery. The eye drops are typically a combination of antibiotics, steroids, and non-steroidal anti-inflammatory medications. Normally, the drops are used 3-4 times per day for up to one month. This poses several problems including, but not limited to, potential non-compliance with the drop schedule, difficulty instilling the drops due to things like arthritis and other common physical ailments found in elderly patients, the high cost of the prescription eye drops, losing or misplacing the eye drops, and others.

Due to the problems present with eye drops, other methods have been introduced. One current method is to inject a compounded formulation (e.g., triamcinolone acetonide and moxifloxacin hydrochloride) into the posterior segment of the eye during surgery. However, properly injecting the formulation into the posterior portion of the eye is not only difficult, but increases the risk of other complications, such as zonular dehiscence, posterior pressure, and retinal toxicity or detachment, among others. For these reasons, post-operative eye drops have remained the standard.

In an effort to overcome these problems, the inventor disclosed, in the earlier parent application, an antibiotic solution and method of injecting the solution into the anterior portion of the eye. While this method has proven effective, additional problems became apparent. For example, both the aqueous humor and the antibiotic solutions are clear fluids. As a result, it can be difficult to determine how much of the antibiotic solution has entered the eye and whether it has been injected into the correct areas. Further, it is impossible to determine whether any of the antibiotic fluid has leaked from the eye. Due to the above problems, it is difficult to ensure accurate dosing, which means that surgeons are less likely to use the method. Accordingly, there remains a need for an antibiotic solution and method of delivery that reduces the risk of endophthalmitis in patients, eliminates patient error and cost to patient, that does not require posterior injections into the eye, and that allows a surgeon to quickly and easily determine that: 1) the antibiotic solution has penetrated the eye in the correct area; and 2) the antibiotic solution has not leaked from the eye. The present disclosure seeks to solve these and other problems.

SUMMARY OF EXAMPLE EMBODIMENTS

In one embodiment, an antibiotic solution for injecting into an eye during an intraoperative procedure comprises 0.1% (1 mg/ml) solution of moxifloxacin and 100-1000 mg/ml of cyanocobalamin (vitamin B12). In one embodiment, the antibiotic solution comprises cyanocobalamin, hydroxocobalamin, methylcobalamin, adenosylcobalamin, or any combination thereof. Because of the cobalt molecules, cobalamins are distinctively red in color. As a result, the antibiotic solution is red in color, making it easily visible against the aqueous humor.

In one embodiment, an antibiotic solution for injecting into an eye during an intraoperative procedure comprises 1% (10 mg/ml) solution of cefuroxime and 100-1000 mg/ml of cyanocobalamin.

In one embodiment, an antibiotic solution for injecting into an eye during an intraoperative procedure comprises 1% (10 mg/ml) solution of vancomycin and 100-1000 mg/ml of cyanocobalamin.

In one embodiment, an antibiotic solution comprises moxifloxacin, cefuroxime, vancomycin, or some combination thereof, and a coloring agent. In one embodiment, the coloring agent is a cobalamin. In one embodiment, the coloring agent may be a vital dye. In one embodiment, the coloring agent may be any substance that is compatible with the aqueous humor.

In one embodiment, a method of preventing post-operative endophthalmitis comprises injecting the colored antibiotic solution into the anterior segment of the eye during surgery, the antibiotic solution comprising moxifloxacin, cefuroxime, vancomycin, or some combination thereof.

DETAILED DESCRIPTION OF EXAMPLE EMBODIMENTS

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrases "in one embodiment" or "in an embodiment" do not necessarily refer to the same embodiment, although they may.

Accordingly, the particular arrangements disclosed are meant to be illustrative only and not limiting as to the scope of the invention. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence or arrangement. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

As discussed in the background section, there is a need for an antibiotic solution and method of delivery that reduces the risk of endophthalmitis in patients, eliminates patient error and cost to patient, that does not require posterior injections into the eye, and that allows a surgeon to quickly and easily determine that: 1) the antibiotic solution has penetrated the eye in the correct area; and 2) the antibiotic solution has not leaked from the eye. As will be understood from the following description, the solutions and methods described herein solve those problems and others.

In one embodiment, an antibiotic solution for injecting into an eye during an intraoperative procedure comprises moxifloxacin and a cobalamin. The cobalamin may be hydroxocobalamin, methylcobalamin, adenosylcobalamin or any combination. In one embodiment, the antibiotic solution comprises 0.1% (1 mg/ml) solution of moxifloxacin (INN—International Nonproprietary Name). Moxifloxacin has the following structure:

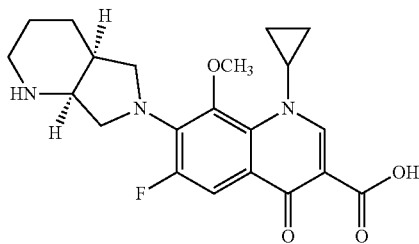 [SMILES: COc1c(N2C[C@@H]3CCCN[C@@H]3C2)c(F)cc2c(=O)c(C(=O)O)cn(C3CC3)c12]

Further details regarding the structure, preparation, and physical properties of moxifloxacin are provided in U.S. Pat. Nos. 4,990,517 and 5,607,942, and German application DE19937116, all of which are incorporated herein by reference. In one embodiment, the antibiotic solution may comprise 100-1000 mg/ml of cyanocobalamin, or an amount sufficient to tint or color the resulting antibiotic solution. The antibiotic solution may further comprise any suitable carrier fluid (e.g., liquid diluents such as water, ethyl alcohol, or propylene glycol), so long as the resulting solution has osmotic values that are compatible with the aqueous humor of the eye and ophthalmic tissues. In one embodiment, the antibiotic solution is prepared and stored in a single-dose vial, without the need for preservatives. This allows the surgeon to provide an accurate concentration in sterile environments. Further, due to the antibiotic solution comprising cyanocobalamin, the resulting antibiotic solution is red in color. This provides a visual enhancement to the surgeon when injecting into the eye. For example, a surgeon would inject around 0.3 milliliters of the antibiotic solution (e.g., solution comprising moxifloxacin and cyanocobalamin) into the anterior segment of the eye during the intraoperative portion of cataract surgery. Because of the red color, the surgeon can easily determine that the injection is placed appropriately and whether any of the antibiotic solution has leaked from the eye. Unlike vital dyes, which stain ocular tissues and must be flushed, the red-colored (cyanocobalamin) antibiotic solution does not stain tissues and is left in the eye (i.e., not flushed). As a result, risk of inflammation and endophthalmitis is lowered or eliminated, without the need for the patient to self-administer antibiotic drops Eliminating patient error significantly decreases the likelihood of endophthalmitis. Further, because the injection is into the anterior segment of the eye, the procedure is very simple for a surgeon to perform and reduces the risks of complications that can occur when injecting into the posterior segment of the eye. As such, the present method is a notable improvement over the prior art. Moxifloxacin has been used orally, intravenous, and topically on the eye. However, moxifloxacin has not been used or indicated for injections into the anterior segment of the eye, and is marketed in the art as topical use only for the eye (e.g., eye drops). Nonetheless, beneficial—even surprising—results are achieved when injecting moxifloxacin into the anterior segment of the eye, with the risk of endophthalmitis being significantly reduced or eliminated altogether. Further, other routes of administration of moxifloxacin, or other antibiotics, for the purpose of treating endophthalmitis have proven ineffective. This is due to the blood-ocular barrier, which prevents adequate amounts of antibiotic from penetrating the eye. Accordingly, the method disclosed herein of direct injection into the anterior segment of the eye solves this problem.

As mentioned, the surgeon does not flush the eye or otherwise remove the red coloration of the antibiotic solution from the aqueous humor. Instead, the cyanocobalamin will be absorbed into the bloodstream in the same manner as the aqueous humor. Leaving the coloring agent in the eye is contrary to any teaching in the art. In other words, surgeons have long used dyes like indocyanine green, fluorescein, and trypan blue to stain the anterior capsule in order to facilitate surgical procedures. For example, after opening the eye for cataract surgery, it is recommended that an air bubble be injected into the anterior chamber of the eye in order to minimize dilution of the vital dye by the aqueous humor. Trypan blue is then applied to the anterior lens capsule using a blunt cannula. The anterior chamber is then irrigated with a balanced salt solution to remove any excess dye, after which the capsulotomy is performed. The vital dyes are meant to stain tissues, and any excess dye should be immediately flushed. In contrast, the antibiotic solution is not meant to stain tissues, nor is it flushed from the eye. Rather, the colored antibiotic solution is injected into the aqueous humor of the eye and left to be absorbed by the bloodstream. There is nothing in the art that teaches or suggests a colored solution or dye of any type that is injected into the aqueous humor of the anterior segment of the eye and that remains post-surgery. Further, leaving the colored antibiotic solution in the eye post-surgery is also contrary to standard practice of using dyes—which require flushing.

While the example of 0.3 milliliters was used above, it will be appreciated that the amount injected may vary, depending upon the concentration of moxifloxacin in the solution. Preferably, the antibiotic solution comprises a range of 200-600 micrograms of moxifloxacin. In the above example, where 0.3 milliliters of 0.1% (1 mg/ml) solution of moxifloxacin was injected, the total concentration of moxifloxacin injected into the eye is 300 micrograms. Nonetheless, other concentrations of moxifloxacin, from 200 micrograms to 600 micrograms, have been shown to be effective in preliminary results. Accordingly, in the examples above, the amount injected may vary depending upon the concentration of moxifloxacin and upon the dosage amount desired. Further, while cyanocobalamin was used in several examples, other cobalamins may also be used. For example, the antibiotic solution may comprise cyanocobalamin, hydroxocobalamin, methylcobalamin, adenosylcobalamin, or any combination thereof. Further, while cobalamins may be the preferred coloring agent, other coloring agents may be used, so long as the coloring agents are compatible with the aqueous humor and do not stain ocular tissues. In one embodiment, a vital dye may be used as a coloring agent, so long as the amount of vital dye introduced into the eye does not stain tissues. Further, the term "coloring" does not mean that the resulting antibiotic solution must be opaque. To the contrary, the resulting antibiotic solution need only be tinted enough to contrast with the clear aqueous humor of the eye.

While the antibiotic solution described above contemplates the use of moxifloxacin, it will be appreciated that other antibiotics, either individually or in combination, may be used. In one embodiment, an antibiotic solution for injecting into the anterior segment of an eye during an intraoperative procedure comprises 1% (10 mg/ml) solution of cefuroxime. Cefuroxime has the following structure:

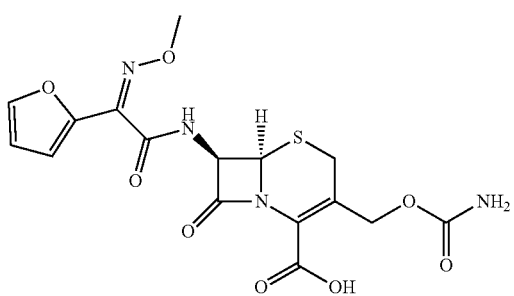 [SMILES: CO/N=C(\C(=O)N[C@@H]1C(=O)N2C(C(=O)O)=C(COC(N)=O)CS[C@H]12)c1ccco1]

In one embodiment, an antibiotic solution for injecting into the anterior segment of an eye during an intraoperative procedure comprises 1% (10 mg/ml) solution of vancomycin. Vancomycin has the following structure:

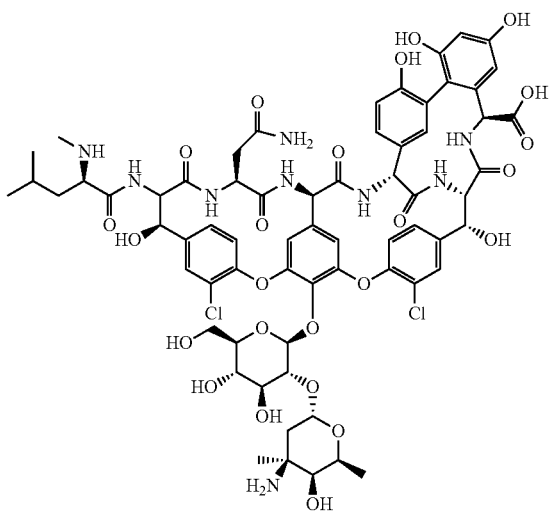 [SMILES: CN[C@H](CC(C)C)C(=O)NC1C(=O)N[C@@H](CC(N)=O)C(=O)N[C@H]2C(=O)N[C@H]3C(=O)N[C@H](C(=O)N[C@H](C(=O)O)c4cc(O)cc(O)c4-c4cc3ccc4O)[C@H](O)c3ccc(c(Cl)c3)Oc3cc2cc(c3O[C@@H]2O[C@H](CO)[C@@H](O)[C@H](O)[C@H]2O[C@H]2C[C@](C)(N)[C@H](O)[C@H](C)O2)Oc2ccc(cc2Cl)[C@H]1O]

The above-mentioned solutions are prepared in the customary manner by known methods, such as by mixing the active antibiotic or compounds with an excipient or excipients (e.g., liquid diluents such as water, ethyl alcohol, or propylene glycol), along with the coloring agent. The final solution may then be sealed and stored in single-use vials known in the industry, which are preferably tinted glass, although other suitable methods and storage vials are not exempted herefrom. Other antibiotic solutions suitable for injection into the eye are disclosed in U.S. patent application Ser. No. 15/148,574 (publication US20160243031A1), titled "Pharmaceutical ophthalmic compositions and methods for fabricating thereof," which is incorporated by reference herein in its entirety.

In one embodiment, a method of preventing post-operative endophthalmitis comprises injecting a colored antibiotic solution into the anterior segment of the eye during surgery, the antibiotic solution comprising moxifloxacin, cefuroxime, vancomycin, or some combination thereof, and a coloring agent. In one embodiment, the coloring agent comprises a cobalamin. It will be appreciated that the antibiotic solution described herein may be used on both humans and animals.

The antibiotic solutions of the present invention may also comprise one or more anti-inflammatory agents, which can be steroidal or non-steroidal. An example of steroidal anti-inflammatory agents for use herein are glucocorticoids.

As is clear from the above disclosure, the antibiotic solution and method of delivery solve the problems in the industry; namely, ease of administration by a surgeon (including increased confidence in proper dosing due to the color contrast), decreased risk of surgical complications, decreased risk of endophthalmitis, and reduced cost and burden to a patient and their insurer. Without a coloring agent, ensuring accurate and consistent dosing from surgery to surgery is difficult, if not impossible. Accordingly, adding a coloring agent, such as cyanocobalamin, provides a contrast in color between the antibiotic solution and the aqueous humor, allowing a surgeon to confidently know placement and dosage, as well as determine leakage.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A method of visualizing the amount of an antibiotic solution administered into an anterior segment of an eye for preventing endophthalmitis, the method comprising:
    injecting the antibiotic solution into the aqueous humor of the anterior segment of the eye, wherein the antibiotic solution comprises a coloring agent to contrast the aqueous humor of the eye which provides for visualization of the antibiotic solution within the eye; the coloring agent remaining inside the eye after injection until it is absorbed or cleared from the eye by the bloodstream or the eye tissues.

2. The method of claim 1, wherein the antibiotic solution comprises moxifloxacin.

3. The method of claim 2, wherein the antibiotic solution injected into the eye comprises a range of 200 to 600 micrograms of moxifloxacin.

4. The method of claim 1, wherein the antibiotic solution comprises cefuroxime.

5. The method of claim 1, wherein the antibiotic solution comprises vancomycin.

6. The method of claim 1, wherein the antibiotic solution comprises a combination of moxifloxacin, cefuroxime, and vancomycin.

7. The method of claim 1, wherein the antibiotic solution comprises an anti-inflammatory agent.

8. A method of visualizing the amount of an antibiotic solution administered into an anterior segment of an eye for preventing endophthalmitis, the method comprising:
    injecting the antibiotic solution into the aqueous humor of the anterior segment of the eye, wherein the antibiotic solution comprises a coloring agent to contrast the aqueous humor of the eye in real time which provides for visualization of the antibiotic solution within the eye; the coloring agent remaining inside the eye after injection until it is absorbed or cleared from the eye by the bloodstream or the eye tissues.

9. A method of visualizing the amount of an antibiotic solution administered into an anterior segment of an eye for preventing endophthalmitis, the method comprising:
    injecting the antibiotic solution into the aqueous humor of the anterior segment of the eye, the antibiotic solution comprising a coloring agent to contrast the aqueous humor of the eye;
    while injecting the antibiotic solution, visualizing the placement and amount of the antibiotic solution in the aqueous humor via the coloring agent; and
    leaving the coloring agent inside the aqueous humor after injection.

* * * * *